United States Patent

Plant Pat. 3,976

Patented Nov. 16, 1976

1

3,976

PEACH TREE

Claron O. Hesse, Kingsburg, Calif., assignor to The Regents of the University of California, Berkeley, Calif.

Filed Oct. 20, 1975, Ser. No. 624,149

Int. Cl.[2] A01H 5/03

U.S. Cl. Plt.—43 1 Claim

Figure 1:
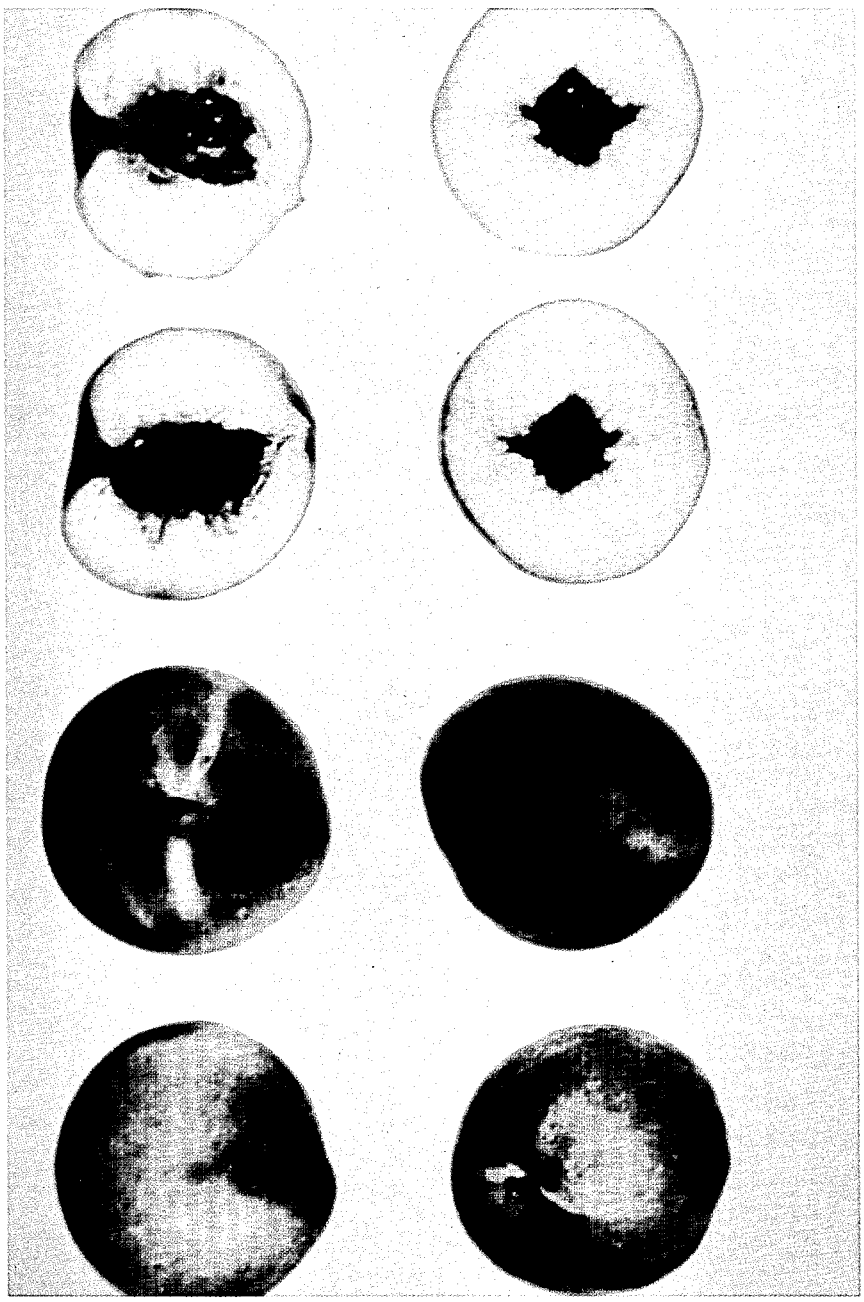

This invention relates to a new and distinct variety of peach tree which is the result of a cross between Fay Elberta and Lippiatt Seedling $29F_3$. The individuals involved in reaching this selection, which has been designated E 3-46 and previously known as the $F_5$, were: $F_1$, SS 13A 21; $F_2$, 17-13, $F_3$, 16-3B; and $F_4$, Da40-17. The last self-pollination was made in 1965.

The E 3–46 selection was discovered in 1960 and was subsequently grown and asexually multiplied at the Kearney Horticultural Field State in 1965. In 1972 it was placed in several authorized grower-cooperative trial plots and tested. The fruit of this new variety ripens a few days after Fayette (unpatented) and before Rio Oso Gem (unpatented).

FIG. 1 of the accompanying drawing illustrates peaches of the new variety which are typical in size, shape and color, some of which are shown in half sections, pitted and unpitted, and in which some of the variations in the size and shape of the fruit, its pit, and the color of the skin and flesh of this variety are indicated.

This new variety is distinguished by the development of fruit having a good blush over the exposed fruit surface, over a deep amber-yellow ground color by the time the fruit has reached shipping maturity, and is further characterized by becoming completely red-blushed by the time it is tree ripe. The fruit is of excellent eating quality having a flavor which is rich, aromatic and sprightly subacid.

The varietal characteristics of this new peach tree described below in detail were observed upon its discovery and subsequently through its test period. The color terminology as used herein is in accordance with Ridgway, Color Standards and Color Nomenclature (1912 Edition).

Tree:

*Size.*—Medium, vigor medium; upright spreading with shape and density determined by pruning.

*Current seasons shoots.*—Applegreen, Plate XVII, tinged with red where exposed.

*Trunk.*—Medium stout; moderately rough; brown (Olive Brown, Plate XI).

*Branches.*—Brown to reddish brown (Sayal Brown, Plate XXIX to Snuff Brown, Plate XXIX); bark rough, peeling off in small recurved platelets which adhere tightly. On younger branches growth cracks longitudinally stirated, showing light brown beneath (Snuff Brown, Plate XXIX).

*Lenticels.*—Numerous, medium size; rather pronounced with raised lips.

*Flower buds.*—Plump, pubescent.

Flowers: 1–2 per node.

*Pedicels.*—Short, 2–3 mm.; medium stout, greenish (Scheele's Green, Plate VI) or tinged red (Bordeaux, Plate XII).

*Corolla.*—Obconic, surface rugose especially apically; usually reddish throughout. Glabrous. Nectaries, greenish orange at anthesis to deep orange (Mignonette Green, Plate XXXI to Deep Chrome, Plate III) with age. Surface more or less irregularly grooved and furrowed to nearly smooth. Extending to near insertion of staments.

2

*Calyx.*—Lobes ovate but slightly separated. Pubescent dorsally and marginally, glabrous ventrally. Red dorsally (Bordeaux, Plate XII); green ventrally (Scheele's Green, Plate VI) or with some reddening basally along the veins with age. Cupped; reflexed 80–90° at full anthesis. Margins entire, usually with a small tipped gland near the apex. Approximately 6 mm. long x 5 mm. wide at base.

*Petals.*—Oval to broad oval, slightly cupped; barely overlapping at full bloom. The basal claw short, medium stout. 19.6±2.7 mm. long x 16.0±1.00 wide. Margins entire or slightly eroded medianly and slightly wavy; occasionally notched near, but not at, apex. Color clear pink (Rose Pink, Plate XII) throughout at anthesis, becoming rosaceous (Pansy Purple, Plate XII) basally with age. Slowly phenotype.

*Stamens.*—Anthers: Slightly small, plump, tending to be rather light reddish throughout dorsally (Carmine, Plate I), and red to buff ventrally (Carmine, Plate I, to Orange Buff, Plate III). Pollen abundant, yellow (Lemon Chrome, Plate IV), fertile. Filaments: Near white to very slightly rosy (Rose Color, Plate XII) at anthesis becoming rosaceous with age and deeper basally. To 18 mm.–20 mm. long. Equal to style.

*Pistil.*—Long; to 18 mm.; greenish. Ovary small, ovate; heavily pubescent; style heavily pubescent basally and becoming less so up to ⅔ of its length, than glabrous; stigma capitate.

Leaves: Midshoot leaves from shoots 18–24″ length.

*Size.*—Medium; 18.5±1.25 cm. long x 4.0±0.21 cm. wide including petiole.

*Shape.*—Ovate-lanceolate to lanceolate; slightly recurved.

*Blade.*—Medium thickness; dark green above (Empire Green, Plate XXXII), slightly lighter below; margin crenate, slightly wavy; blade flat to slightly folded. Midrib very lightly puberulent next to the blade; Yellow-Green, Plate VI.

*Petiole.*—Short, stout; 1.02±0.08 cm. long. Rather shallowly grooved on upper side.

*Glands.*—2–5, borne apically on petiole or on base of blade, globose.

Fruit:

*Ripe.*—August 13, in 1973, tree ripe.

*Crop.*—Full crop.

*Size.*—Medium; 77.20±2.60 mm. long x 79.51±3.58 mm. cheek diameter x 76.80±2.96 mm. suture diameter. Average weight of fruit 248±26.27 gms.

*Shape.*—Broad elliptic, truncate at the base, the base sloping toward the ventral suture rather markedly, the apex rounded; the dorsal side somewhat longer. Regular, uniform. Ventral suture aspect: Broad elliptic to broad ovate, occasionally round or nearly so; nearly symmetrical or with one half slightly larger. Axial aspect: round or nearly so; the ventral half slightly larger.

*Base.*—Medium size, flat; sloping toward the ventral suture.

*Cavity.*—Round or broad oval, smooth and regular. Slightly and broadly depressed at the dorsal edge; very shallowly or not at all depressed at the ventral edge. Medium-shallow depth; usually flaring broad conic; occasionally narrower and conic.

*Shoulders.*—Smoothly rounded to the cavity; occasionally very lightly creased at the ventral suture.

*Suture.*—A very shallow narrow groove from the base to the apex, or occasionally a line basally. Only slightly deeper apically; occasionally running a short distance beyond the stylar scar, but usually only lightly depressed dorsal to the stylar scar. Often slightly rough. One-half often somewhat larger, especially apically, forming a lip which is rather narrow and close to the suture.

*Apex.*—Rounded, symmetrical to the long axis of the fruit; terminating in a low fleshy tip. The stylar scar a dot.

*Color.*—Ground color amber-yellow (golden) (Plate XVI). Blush: Medium red (Nopal Red, Plate I), washed; solid to semiwashed covering the entire surface except where the fruit is compressed against the shoot. The more exposed surfaces a solid darker red (Ox-Blood Red, Plate I). The shaded surfaces semi-washed with some deeper, rather obscure, irregular blotching of deeper red (Ox-Blood Red, Plate I). Often obscurely and finely streaked deeper red near the sutures.

*Pubscence.*—Medium in amount; moderately short.

*Flesh Color.*—Rich golden yellow (Appricot Yellow, Plate IV) throughout. Red in the flesh only next to the cavity.

*Cavity Color.*—Sprightly medium red (Carmine, Plate I) with some surface whitish callous.

*Adhesion.*—Air free, the cavity somewhat larger than the stone apically.

*Flesh.*—Firm when full ripe; firm-melting. Texture medium, moderately fine.

*Flavor.*—Rich, aromatic, sprightly subacid, excellent.

*Stone.*—Medium size; 35.4±0.87 mm. long x 17.35 ±1.27 mm. thick x 23.38±0.81 mm. wide; elliptic to slightly obovate; symmetrical to somewhat asymmetrical with the dorsal edge longer. The base more or less broadly, but slightly necked, at right angles to the stone axis, or sloping somewhat toward the ventral edge. The stem scar medium, elliptic. The ventral edge low-rounded; the suture inconspicuously eroded. The wings close, low, more or less interrupted and eroded; blunt. The lateral grooves of medium depth, rounded. The dorsal sutures often raised; channeled, the channel of medium or less depth with the sides more or less interrupted; blunt to sharp. The apex a rather blunt, short, more or less eroded tip; occasionally acuminate and sharp tipped. The lateral surfaces pitting and grooving rather variable. Often mostly pitted except apically; the pits and grooves usually rather shallow. The groove edges blunt, rounded. Color brown (Kaiser Brown, Plate XIV), stained bright red (Carmine, Plate I) at the base only.

*Seed.*—Long elliptic to slightly ovate; testas brown (Sanford's brown, Plate II). Moderately plump.

I claim:

1. The new and distinct variety of peach tree herein described and illustrated, and identified by the characteristics enumerated above.

No references cited.

ROBERT E. BAGWILL, Primary Examiner